United States Patent
Wessel et al.

(10) Patent No.: US 9,574,177 B2
(45) Date of Patent: Feb. 21, 2017

(54) METHODS FOR REDUCING AND/OR PREVENTING EXCESSIVE CELLULAR APOPTOSIS

(71) Applicant: Stemnion, Inc., Pittsburgh, PA (US)

(72) Inventors: Howard C Wessel, New Kensington, PA (US); Richard A Banas, Turtle Creek, PA (US)

(73) Assignee: STEMNION, INC., Pittsburgh, PA (US)

( * ) Notice: Subject to any disclaimer, the term of this patent is extended or adjusted under 35 U.S.C. 154(b) by 0 days.

(21) Appl. No.: 14/619,241

(22) Filed: Feb. 11, 2015

(65) Prior Publication Data

US 2015/0152383 A1 Jun. 4, 2015

Related U.S. Application Data

(63) Continuation of application No. 13/956,580, filed on Aug. 22, 2013, now abandoned.

(60) Provisional application No. 61/679,150, filed on Aug. 3, 2012, provisional application No. 61/768,429, filed on Feb. 23, 2013.

(51) Int. Cl.

| | |
|---|---|
| *C12N 5/0783* | (2010.01) |
| *C12N 5/073* | (2010.01) |
| *C12N 5/0789* | (2010.01) |
| *C12N 5/077* | (2010.01) |
| *A61K 38/17* | (2006.01) |
| *A61K 35/12* | (2015.01) |
| *A61K 38/18* | (2006.01) |

(52) U.S. Cl.
CPC ............ *C12N 5/0636* (2013.01); *A61K 35/12* (2013.01); *A61K 38/1793* (2013.01); *A61K 38/1866* (2013.01); *C12N 5/0605* (2013.01); *C12N 5/0647* (2013.01); *C12N 5/0656* (2013.01); *C12N 2501/135* (2013.01); *C12N 2501/15* (2013.01); *C12N 2501/165* (2013.01); *C12N 2501/40* (2013.01); *C12N 2501/48* (2013.01); *C12N 2501/73* (2013.01); *C12N 2502/025* (2013.01)

(58) Field of Classification Search
None
See application file for complete search history.

(56) References Cited

U.S. PATENT DOCUMENTS 8,197,804 B2 * 6/2012 Sing ............... A61K 35/48
424/93.1

OTHER PUBLICATIONS

Adrie, C. et al. 2010. Immune status and apoptosis activation during brain death. Shock 33(4): 353-362.specif. p. 353.*
Steed, D., et al., ePlasty (2008) 8:157-165.
Rehman, J., et al., Circulation (2012) 109:1292-1298.
Menke, N., et al., Clinics in Dermatology (2007) 25:19-25.
Hung, S., et al., Stem Cells (2007) 25:2363-2370.
Gerber, H., et al., Journal of Biological Chemistry (1998) 273 (46):30336-30343.
Fuchs, C., et al., Investigative Ophthalmology and Isual Science (2005) 46:2943-2991.
Elsasser, A., et al., Journal Molecular Cell Cardiology (2000) 32:711-724.
Abouna, G.M., Transplantation Proceedings (2008) 40:34-38.
Boulday, G., et al., Annals of the New York Academy of Science (2004) 1030:28-36.
Lim, M., et al., Annals of the New York Academy of Science (1999) 878.1:522-523.
Presciutti, S.M., et al., Journal of Orthopedic Research (2014) 32 (9):1181-1188.

* cited by examiner

*Primary Examiner* — Renee Claytor
*Assistant Examiner* — Sharon M Papciak
(74) *Attorney, Agent, or Firm* — Linda O. Palladino; Gail M. Kempler

(57) ABSTRACT

The invention is directed to methods for reducing the number of apoptotic cell deaths in a population of cells undergoing excessive cellular apoptosis. The invention is also directed to methods for preventing apoptotic cell death in a population of cells at risk for developing excessive cellular apoptosis. In particular, the invention is directed to methods for reducing or preventing excessive cellular apoptosis comprising exposing cells exhibiting or at risk for developing excessive cellular apoptosis to a cellular factor-containing composition called Amnion-derived Cellular Cytokine Solution (referred to herein as ACCS), which is obtained from the culturing of Amnion-derived Multipotent Progenitor (AMP) cells, or AMP cells.

11 Claims, No Drawings

METHODS FOR REDUCING AND/OR PREVENTING EXCESSIVE CELLULAR APOPTOSIS

CROSS-REFERENCE TO RELATED APPLICATIONS

This application is a continuation application of U.S. application Ser. No. 13/956,580, filed Aug. 22, 2013 and claims priority under 35 USC §119(e) of U.S. Provisional Application No. 61/679,150, filed Aug. 3, 2012 and U.S. Provisional Application No. 61/768,429, filed Feb. 23, 2012, the entireties of which are incorporated herein by reference.

STATEMENT REGARDING FEDERALLY SPONSORED RESEARCH OR DEVELOPMENT

This invention was made in part with United States government support awarded by the following agency: Naval Medical Logistics Command, Contract #N62645-11-1-001. The United States may have certain rights to this invention.

FIELD OF THE INVENTION

The field of the invention is directed to novel methods for reducing the number of apoptotic cell deaths in a population of cells undergoing excessive cellular apoptosis. The field of the invention is also directed to novel methods for preventing apoptotic cell death in a population of cells at risk for developing excessive cellular apoptosis. In particular, the field of the invention is directed to novel methods for reducing or preventing excessive cellular apoptosis comprising exposing cells exhibiting or at risk for developing excessive cellular apoptosis to a novel cellular factor-containing composition called Amnion-derived Cellular Cytokine Solution (referred to herein as ACCS), which is obtained from the culturing of Amnion-derived Multipotent Progenitor (AMP) cells. The field of the invention is also directed to novel methods for reducing or preventing excessive cellular apoptosis comprising exposing cells exhibiting or at risk for developing excessive cellular apoptosis to Amnion-derived Multipotent Progenitor (AMP) cells.

BACKGROUND OF THE INVENTION

As reviewed in Susan Elmore, Toxicol Pathol. 2007; 35(4): 495-516, apoptosis occurs normally during development and aging and as a homeostatic mechanism to maintain cell populations in tissues. Apoptosis also occurs as a defense mechanism such as in immune reactions or when cells are damaged by disease or noxious agents (Norbury and Hickson, 2001). Although there is a wide variety of stimuli and conditions, both physiological and pathological, that can trigger apoptosis, not all cells will necessarily die in response to the same stimulus. Irradiation or drugs used for cancer chemotherapy results in DNA damage in some cells, which can lead to apoptotic death through a p53-dependent pathway. Some hormones, such as corticosteroids, may lead to apoptotic death in some cells (e.g., thymocytes) although other cells are unaffected or even stimulated. Some cells express Fas or TNF receptors that can lead to apoptosis via ligand binding and protein cross-linking. Other cells have a default death pathway that must be blocked by a survival factor such as a hormone or growth factor. There is also the issue of distinguishing apoptosis from necrosis, two completely different processes that can occur independently, sequentially, as well as simultaneously (Hirsch, 1997; Zeiss, 2003). Generally, necrosis is the result of acute injury to the cell, whereas apoptosis is controlled by a diverse group if signals that can be either intrinsic (intracellular) or extrinsic (extracellular). Finally, apoptosis is a coordinated and often energy-dependent process that involves the activation of a group of cysteine proteases called "caspases" and a complex cascade of events that link the initiating stimulus to the final demise of the cell.

Many pathological conditions feature excessive cellular apoptosis (i.e., neurodegenerative diseases, AIDS, ischemia, radiation exposure, to name a few) and thus may benefit from therapeutically preventing or reducing apoptosis-induced cell death. For example, excessive cellular apoptosis is thought to play an important role in myocardial ischemia caused by an insufficient blood supply, leading to a decrease in oxygen delivery to, and subsequent death of, the cardiomyocytes. The methods of the invention may be useful to prevent or reduce the number of cardiomyocytes undergoing apoptosis-induced death.

BRIEF SUMMARY OF THE INVENTION

Applicants present herewith for the first time the instant invention whose object is to reduce the number of apoptosis-induced cell deaths in a population of cells undergoing excessive cellular apoptosis and also to prevent apoptosis-induced cell death in a population of cells at risk for developing excessive cellular apoptosis. To accomplish this, Applicants utilize a novel cellular factor-containing composition referred to herein as "Amnion-derived Cellular Cytokine Solution" or "ACCS". ACCS contains a unique and complex combination of physiologic levels of cytokines, growth factors and other protein factors that are found naturally in the body. In addition, antibody array data demonstrates that ACCS contains numerous anti-apoptotic factors such as Bcl-2 (B-cell lymphoma 2), Bcl-w, CD40L (CD40 Ligand), cIAP-2, HSP60 (heat shock protein 60), HSP70 (heat shock protein 70), IGF-II (Insulin growth factor II), IGF-1sR (IGF-1 soluble receptor), Livin, P27 (cyclin Kinase inhibitor), Survivin, sTNF-R1, sTNF-R2, TRAILR-3, TRAILR-4. Thus ACCS may exhibit anti-apoptotic effects across a broad array of cell types. To demonstrate this anti-apoptotic activity, Applicants tested human foreskin fibroblasts (HFFs) and Jurkat cells in a standard anti-apoptotic assay.

It is also an object of the instant invention to utilize Amnion-derived Multipotent Progenitor (AMP) cells, which produce ACCS, in the claimed methods.

Accordingly, a first aspect of the invention is a method for reducing the number of apoptosis-induced cell deaths in a population of cells undergoing excessive cellular apoptosis, the method comprising the step of contacting the population of cells undergoing excessive cellular apoptosis with a therapeutically effective dose of a composition selected from the group consisting of Amnion-derived Cellular Cytokine Solution (ACCS) and Amnion-derived Multipotent Progenitor (AMP) cells, such that the number of apoptosis-induced cell deaths is reduced.

A second aspect of the invention is a method of protecting a population of cells at risk for developing excessive cellular apoptosis, the method comprising the step of contacting the population of cells at risk for developing excessive cellular apoptosis with a therapeutically effective dose of a composition selected from the group consisting of ACCS and AMP cells, such that the cells are protected from developing excessive cellular apoptosis.

In one embodiment of the method of aspect one and two the ACCS comprises physiologic concentrations of VEGF, TGFβ2, Angiogenin, PDGF, TIMP-1 and TIMP-2. In a specific embodiment the physiologic concentration is about 5.0-16 ng/mL for VEGF, about 3.5-4.5 ng/mL for Angiogenin, about 100-165 pg/mL for PDGF, about 2.5-2.7 ng/mL for TGFβ2, about 0.68 μg/mL for TIMP-1, and about 1.04 μg/mL for TIMP-2.

In another embodiment of the method of aspect one and two the excessive cellular apoptosis occurs in a subject as a result of a condition selected from the group consisting of an ischemic condition, a radiation-induced injury, and an injury to nervous tissue.

In another embodiment of the method of aspect one the excessive cellular apoptosis occurs in an organ or tissue as a result of an ischemic condition.

In another embodiment of the method of aspect two the protecting of cells from excessive cellular apoptosis occurs in an organ or tissue that is at risk of developing an ischemic condition. In a specific embodiment, the organ or tissue is a donated organ or tissue.

In another embodiment of aspect one and two the ACCS or AMP cells are administered in combination with another agent. In a specific embodiment the other agent is selected from the group consisting of cytokines, chemokines, growth factors, antibodies, inhibitors, antibiotics, anti-fungals, anti-virals, immunosuppressive agents, anti-oxidants and other cell types.

The above-described aspects and embodiments of the invention are not intended to be limiting, but rather exemplary. Skilled artisans will recognize that additional aspects and embodiments of the invention, though not explicitly or specifically described, are contemplated and encompassed by the teachings and examples set forth in the specification.

Definitions

As defined herein "isolated" refers to material removed from its original environment and is thus altered "by the hand of man" from its natural state.

As used herein, "enriched" means to selectively concentrate or to increase the amount of one or more materials by elimination of the unwanted materials or selection and separation of desirable materials from a mixture (i.e. separate cells with specific cell markers from a heterogeneous cell population in which not all cells in the population express the marker).

As used herein, the term "substantially purified" means a population of cells substantially homogeneous for a particular marker or combination of markers. By substantially homogeneous is meant at least 90%, and preferably 95% homogeneous for a particular marker or combination of markers.

The term "placenta" as used herein means both preterm and term placenta.

As used herein, the term "totipotent cells" shall have the following meaning. In mammals, totipotent cells have the potential to become any cell type in the adult body; any cell type(s) of the extraembryonic membranes (e.g., placenta). Totipotent cells are the fertilized egg and approximately the first 4 cells produced by its cleavage.

As used herein, the term "pluripotent stem cells" shall have the following meaning. Pluripotent stem cells are true stem cells with the potential to make any differentiated cell in the body, but cannot contribute to making the components of the extraembryonic membranes which are derived from the trophoblast. The amnion develops from the epiblast, not the trophoblast. Three types of pluripotent stem cells have been confirmed to date: Embryonic Stem (ES) Cells (may also be totipotent in primates), Embryonic Germ (EG) Cells, and Embryonic Carcinoma (EC) Cells. These EC cells can be isolated from teratocarcinomas, a tumor that occasionally occurs in the gonad of a fetus. Unlike the other two, they are usually aneuploid.

As used herein, the term "multipotent stem cells" are true stem cells but can only differentiate into a limited number of types. For example, the bone marrow contains multipotent stem cells that give rise to all the cells of the blood but may not be able to differentiate into other cells types.

As used herein, the term "Amnion-derived Multipotent Progenitor cell" or "AMP cell" means a specific population of cells that are epithelial cells derived from the amnion. AMP cells have the following characteristics. They have not been cultured in the presence of any non-human animal materials, making them and cell products derived from them suitable for human clinical use as they are not xeno-contaminated. AMP cells are cultured in basal medium supplemented with human serum albumin. In a preferred embodiment, the AMP cells secrete the cytokines VEGF, Angiogenin, PDGF and TGFβ2 and the MMP inhibitors TIMP-1 and/or TIMP-2. The physiological range of the cytokine or cytokines in the unique combination is as follows: about 5-16 ng/mL for VEGF, about 3.5-4.5 ng/mL for Angiogenin, about 100-165 pg/mL for PDGF, about 2.5-2.7 ng/mL for TGFβ2, about 0.68 μg/mL for TIMP-1 and about 1.04 μg/mL for TIMP-2. AMP cells grow without feeder layers, do not express the protein telomerase and are non-tumorigenic. AMP cells do not express the hematopoietic stem cell marker CD34 protein. The absence of CD34 positive cells in this population indicates the cells are not contaminated with hematopoietic stem cells such as umbilical cord blood or embryonic fibroblasts. Virtually 100% of the cells react with antibodies to low molecular weight cytokeratins, confirming their epithelial nature. Freshly isolated amnion-derived cells, from which AMP cells are isolated, will not react with antibodies to the stem/progenitor cell markers c-kit (CD117) and Thy-1 (CD90). Several procedures used to obtain cells from full term or pre-term placenta are known in the art (see, for example, US 2004/0110287; Anker et al., 2005, Stem Cells 22:1338-1345; Ramkumar et al., 1995, Am. J. Ob. Gyn. 172:493-500). However, the methods used herein provide improved compositions and populations of cells.

By the term "animal-free" when referring to certain compositions, growth conditions, culture media, etc. described herein, is meant that no non-human animal-derived materials, such as bovine serum, proteins, lipids, carbohydrates, nucleic acids, vitamins, etc., are used in the preparation, growth, culturing, expansion, storage or formulation of the certain composition or process. By "no non-human animal-derived materials" is meant that the materials have never been in or in contact with a non-human animal body or substance so they are not xeno-contaminated. Only clinical grade materials, such as recombinantly produced human proteins, are used in the preparation, growth, culturing, expansion, storage and/or formulation of such compositions and/or processes.

By the term "expanded", in reference to cell compositions, means that the cell population constitutes a significantly higher concentration of cells than is obtained using previous methods. For example, the level of cells per gram of amniotic tissue in expanded compositions of AMP cells is at least 50 and up to 150 fold higher than the number of amnion epithelial cells in the primary culture after 5 passages, as compared to about a 20 fold increase in such cells using previous methods. In another example, the level of cells per grain of amniotic tissue in expanded compositions of AMP cells is at least 30 and up to 100 fold higher than the number of amnion epithelial cells in the primary culture after 3 passages. Accordingly, an "expanded" population has at least a 2 fold, and up to a 10 fold, improvement in cell numbers per gram of amniotic tissue over previous methods. The term "expanded" is meant to cover only those situations, in which a person has intervened to elevate the number of the cells.

As used herein, the term "passage" means a cell culture technique in which cells growing in culture that have attained confluence or are close to confluence in a tissue culture vessel are removed from the vessel, diluted with fresh culture media (i.e. diluted 1:5) and placed into a new tissue culture vessel to allow for their continued growth and viability. For example, cells isolated from the amnion are referred to as primary cells. Such cells are expanded in culture by being grown in the growth medium described herein. When such primary cells are subcultured, each round of subculturing is referred to as a passage. As used herein, "primary culture" means the freshly isolated cell population.

As used herein, "conditioned medium" is a medium in which a specific cell or population of cells has been cultured, and then removed. When cells are cultured in a medium, they may secrete cellular factors that can provide support to or affect the behavior of other cells. Such factors include, but are not limited to hormones, cytokines, extracellular matrix (ECM), proteins, vesicles, antibodies, chemokines, receptors, inhibitors and granules. The medium containing the cellular factors is the conditioned medium. Examples of methods of preparing conditioned media are described, in U.S. Pat. No. 6,372,494 which is incorporated by reference in its entirety herein.

As used herein, the term "Amnion-derived Cellular Cytokine Solution" or "ACCS" means conditioned medium that has been derived from AMP cells that have been cultured in basal media supplemented with human serum albumin and recombinant human EGF.

The term "physiological level" as used herein means the level that a substance in a living system is found and that is relevant to the proper functioning of a biochemical and/or biological process.

As used herein, the term "solution" as used in "Amnion-derived Cellular Cytokine Solution" means a liquid containing dispersed components, i.e. cytokines. The dispersed components may be fully solubilized, partially solubilized, suspended or otherwise dispersed in the liquid. Suitable liquids include, but are not limited to, water, osmotic solutions such as salt and/or sugar solutions, cell culture media, and other aqueous or non-aqueous solutions.

The term "lysate" as used herein refers to the composition obtained when cells, for example, AMP cells, are lysed and optionally the cellular debris (e.g., cellular membranes) is removed. This may be achieved by mechanical means, by freezing and thawing, by sonication, by use of detergents, such as EDTA, or by enzymatic digestion using, for example, hyaluronidase, dispase, proteases, and nucleases. In some instances, it may be desirable to lyse the cells and retain the cellular membrane portion and discard the remaining portion of the lysed cells.

As used herein, the term "pooled" means a plurality of compositions that have been combined to create a new composition having more constant or consistent characteristics as compared to the non-pooled compositions. For example, pooled ACCS have more constant or consistent characteristics compared to non-pooled ACCS. Examples of pooled compositions include "SP pools" (more than one ACCS collection/one placenta), "MP1 pools" (one ACCS collection/placenta, multiple placentas), and "MP2 pools" (more than one ACCS collection/placenta, multiple placentas).

As used herein, the term "substrate" means a defined coating on a surface that cells attach to, grown on, and/or migrate on. As used herein, the term "matrix" means a substance that cells grow in or on that may or may not be defined in its components. The matrix includes both biological and non-biological substances. As used herein, the term "scaffold" means a three-dimensional (3D) structure (substrate and/or matrix) that cells grow in or on. It may be composed of biological components, synthetic components or a combination of both. Further, it may be naturally constructed by cells or artificially constructed. In addition, the scaffold may contain components that have biological activity under appropriate conditions.

The term "cell product" or "cell products" as used herein refers to any and all substances made by and secreted from a cell, including but not limited to, protein factors (i.e. growth factors, differentiation factors, engraftment factors, cytokines, morphogens, proteases (i.e. to promote endogenous cell delamination, protease inhibitors), extracellular matrix components (i.e. fibronectin, etc.).

The term "therapeutically effective amount" means that amount of a therapeutic agent necessary to achieve a desired physiological effect (i.e. reduce or prevent excessive cellular apoptosis).

As used herein, the term "pharmaceutically acceptable" means that the components, in addition to the therapeutic agent, comprising the formulation, are suitable for administration to the patient being treated in accordance with the present invention.

As used herein, the term "therapeutic protein" includes a wide range of biologically active proteins including, but not limited to, growth factors, enzymes, hormones, cytokines, inhibitors of cytokines, blood clotting factors, peptide growth and differentiation factors.

As used herein, the term "tissue" refers to an aggregation of similarly specialized cells united in the performance of a particular function.

As used herein, the terms "a" or "an" means one or more; at least one.

As used herein, the term "adjunctive" means jointly, together with, in addition to, in conjunction with, and the like.

As used herein, the term "co-administer" can include simultaneous or sequential administration of two or more agents.

As used herein, the term "agent" means an active agent or an inactive agent. By the term "active agent" is meant an agent that is capable of having a physiological effect when administered to a subject. Non-limiting examples of active agents include growth factors, cytokines, antibiotics, cells, conditioned media from cells, etc. By the term "inactive agent" is meant an agent that does not have a physiological effect when administered. Such agents may alternatively be called "pharmaceutically acceptable excipients". Non-limiting examples include time release capsules and the like.

The terms "parenteral administration" and "administered parenterally" are art-recognized and refer to modes of administration other than enteral and topical administration, usually by injection, and includes, without limitation, intravenous, intramuscular, intraarterial, intrathecal, intracapsular, intraorbital, intracardiac, intradermal, intraperitoneal, transtracheal, subcutaneous, subcuticular, intra-articulare, subcapsular, subarachnoid, intraspinal, epidural, intracerebral and intrasternal injection or infusion.

The term "enteral administration" and "administered enterally" are art-recognized and refer to modes of administration other than enteral and topical administration, usually by oral or rectal routes.

The term "topical administration" and "administered topically" are art-recognized and refer to modes of administration other than parenteral and enteral administration, usually by application to the skin or mucous membranes.

The terms "sustained-release", "extended-release", "time-release", "controlled-release", "slow-release", or "continuous-release" as used herein means an agent, typically a therapeutic agent or drug, that is released over time.

As used herein, the term "apoptosis" means a pattern of cell death affecting single cells, marked by shrinkage of the cell, condensation of chromatin, and fragmentation of the cell into membrane-bound bodies that are eliminated by phagocytosis. Apoptosis is often used synonymously with programmed cell death, which is a theory that states that particular cells are programmed to die at, specific sites and at specific stages of development.

As used herein, the term "excessive cellular apoptosis" means that a population of cells is exhibiting a level of apoptosis-induced cell death that is above the homeostatic level of apoptosis-induced cell death normally exhibited by the cell population. Different types of cells will exhibit a homeostatic level of apoptosis-induced cell death that is specific to that cell type.

"Treatment," "treat," or "treating," as used herein covers any treatment of a disease or condition of a mammal, particularly a human, and includes: (a) preventing the disease or condition from occurring in a subject which may be predisposed to the disease or condition but has not yet been diagnosed as having it; (b) inhibiting the disease or condition, i.e., arresting its development; (c) relieving and or ameliorating the disease or condition, i.e., causing regression of the disease or condition; or (d) curing the disease or condition, i.e., stopping its development or progression. The population of subjects treated by the methods of the invention includes subjects suffering from the undesirable condition or disease, as well as subjects at risk for development of the condition or disease.

DETAILED DESCRIPTION

Where a range of values is provided, it is understood that each intervening value, to the tenth of the unit of the lower limit unless the context clearly dictates otherwise, between the upper and lower limit of that range and any other stated or intervening value in that stated range is encompassed within the invention. The upper and lower limits of these smaller ranges may independently be included in the smaller ranges is also encompassed within the invention, subject to any specifically excluded limit in the stated range. Where the stated range includes one or both of the limits, ranges excluding either both of those included limits are also included in the invention.

Unless defined otherwise, all technical and scientific terms used herein have the same meaning as commonly understood by one of ordinary skill in the art to which this invention belongs. Although any methods and materials similar or equivalent to those described herein can also be used in the practice or testing of the present invention, the preferred methods and materials are now described.

It must be noted that as used herein and in the appended claims, the singular forms "a," "and" and "the" include plural references unless the context clearly dictates otherwise.

Compositions and Methods of Making Compositions

Detailed information and methods on the preparation of AMP cell compositions, generation of ACCS, generation of pooled ACCS, detection of cytokines in non-pooled and pooled ACCS using ELISA, generation of PCS compositions, and generation of sustained-release CFS compositions can be found in U.S. Pat. Nos. 8,058,066 and 8,088,732, both of which are incorporated herein by reference.

The compositions of the invention can be prepared in a variety of ways depending on the intended use of the compositions. For example, a composition useful in practicing the invention may be a liquid comprising an agent of the invention, i.e. ACCS, in solution, in suspension, or both (solution/suspension). The term "solution/suspension" refers to a liquid composition where a first portion of the active agent is present in solution and a second portion of the active agent is present in particulate form, in suspension in a liquid matrix. A liquid composition also includes a gel. The liquid composition may be aqueous or in the form of an ointment, salve, cream, or the like.

An aqueous suspension or solution/suspension useful for practicing the methods of the invention may contain one or more polymers as suspending agents. Useful polymers include water-soluble polymers such as cellulosic polymers and water-insoluble polymers such as cross-linked carboxyl-containing polymers. An aqueous suspension or solution/suspension of the present invention is preferably viscous or muco-adhesive, or even more preferably, both viscous and muco-adhesive.

Pharmaceutical Compositions—The present invention provides pharmaceutical compositions of ACCS and a pharmaceutically acceptable carrier. The term "pharmaceutically acceptable" means approved by a regulatory agency of the Federal or a state government or listed in the U.S. Pharmacopeia or other generally recognized pharmacopeia for use in animals, and more particularly, in humans. The term "carrier" refers to a diluent, adjuvant, excipient, or vehicle with which the composition is administered. Such pharmaceutical carriers can be sterile liquids, such as water and oils, including those of petroleum, animal, vegetable or synthetic origin, such as peanut oil, soybean oil, mineral oil, sesame oil and the like. Suitable pharmaceutical excipients include starch, glucose, lactose, sucrose, gelatin, malt, rice, flour, chalk, silica gel, sodium stearate, glycerol monostearate, talc, sodium chloride, dried skim milk, glycerol, propylene, glycol, water, ethanol and the like. The composition, if desired, can also contain minor amounts of wetting or emulsifying agents, or pH buffering agents. These compositions can take the form of solutions, suspensions, emulsion, tablets, pills, capsules, powders, sustained-release formulations and the like. Examples of suitable pharmaceutical carriers are described in "Remington's Pharmaceutical Sciences" by E. W. Martin, and still others are familiar to skilled artisans.

The pharmaceutical compositions of the invention can be formulated as neutral or salt forms. Pharmaceutically acceptable salts include those formed with free amino groups such as those derived from hydrochloric, phosphoric, acetic, oxalic, tartaric acids, etc., and those formed with free carboxyl groups such as those derived from sodium, potassium, ammonium, calcium, ferric hydroxides, isopropylamine, triethylamine, 2-ethylamino ethanol, histidine, procaine, etc.

Treatment Kits—The invention also provides for an article of manufacture comprising packaging material and a pharmaceutical composition of the invention contained within the packaging material, wherein the pharmaceutical composition comprises ACCS or AMP cells. The packaging material comprises a label or package insert which indicates that the ACCS or AMP cells can be used to reduce or prevent excessive apoptosis-induced cell death in a subject in need thereof.

One of skill in the art may readily determine the appropriate concentration, or dose, of ACCS or AMP cells for a particular purpose. The skilled artisan will recognize that a preferred dose is one which produces a therapeutic effect, for example reducing or preventing excessive apoptosis-induced cell death, in a patient in need thereof. Of course, proper doses of ACCS or AMP cells will require empirical determination at the time of use based on several variables including but not limited to the severity and type of condition being treated; patient age, weight, sex, health; other medications and treatments being administered to the patient; and the like. For example, an exemplary dose of ACCS for infusion into an organ, for example the brain, is about 0.001 mL/hour. An exemplary dose of ACCS for IV administration is between about 2-10 mL/kg of body weight/day. As with any drug, other doses may be appropriate for a given circumstance and/or patient. One of skill in the art will also recognize that number of doses (dosing regimen) to be administered needs also to be empirically determined based on, for example, seventy and type of condition being treated. In a preferred embodiment, one dose is sufficient.

The present invention provides a method of reducing or preventing excessive apoptosis-induced cell death by administering a therapeutically effective dose of ACCS or AMP cells to a subject in need thereof. By "therapeutically effective amount" is meant the dose of ACCS or AMP cells is sufficient to elicit a therapeutic effect. Thus, the concentration of ACCS or AMP cells in an administered dose unit in accordance with the present invention is effective in, for example, reducing or preventing excessive apoptosis-induced cell death.

In further embodiments of the present invention, it may be desirable to co-administer other agents, including active agents and/or inactive agents, with the ACCS or AMP cells to reduce or prevent excessive apoptosis-induced cell death. Active agents include but are not limited to cytokines, chemokines, growth factors, antibodies, inhibitors, antibiotics, anti-fungals, anti-virals, immunosuppressive agents, anti-oxidants, other cell types, and the like. Inactive agents include carriers, diluents, stabilizers, gelling agents, thickening agents (i.e. human serum albumin, hyaluronic acid), delivery vehicles, ECMs (natural and synthetic), scaffolds, collagen, implant devices, and the like. When the ACCS or AMP cells is administered conjointly with other pharmaceutically active agents, even less of the ACCS or AMP cells may be needed to be therapeutically effective.

The timing of administration of the ACCS or AMP cells will depend upon the type and severity of the condition being treated. In a preferred embodiment, the ACCS or AMP cells are administered as soon as possible after the condition occurs.

Exemplary Therapeutic Uses of ACCS or AMP Cells for Reducing or Prevent Excessive Apoptosis-induced Cell Death The following is a non-limiting description of diseases, disorders and injuries in which apoptosis is known to play a role and that may, therefore, benefit from the compositions and methods of the invention described herein.

Acute radiation syndrome (ARS) is a constellation of acute health effects which begin within 24 hours of exposure to high amounts of ionizing radiation. The onset and type of symptoms depends on the radiation exposure. Relatively smaller doses result in gastrointestinal effects such as nausea and vomiting and symptoms related to falling blood counts such as infection and bleeding. Relatively larger doses can result in neurological effects and rapid death. Similar symptoms may appear months to years after exposure as chronic radiation syndrome. Radiation exposure can also increase the probability of developing other diseases, primarily cancers.

Traumatic Brain Injuries (TBI) can result from a closed head injury or a penetrating head injury. A closed injury occurs when the head suddenly and violently hits an object but the object does not break through the skull. A penetrating injury occurs when an object pierces the skull and enters brain tissue. Skull fractures occur when the bone of the skull cracks or breaks. A depressed skull fracture occurs when pieces of the broken skull press into the tissue of the brain. A penetrating skull fracture occurs when something pierces the skull, such as a bullet, leaving a distinct and localized injury to brain tissue. Skull fractures can cause cerebral contusion. Another insult to the brain that can cause injury is anoxia. Anoxia is a condition in which there is an absence of oxygen supply to an organ's tissues, even if there is adequate blood flow to the tissue. Hypoxia refers to a decrease in oxygen supply rather than a complete absence of oxygen, and ischemia is inadequate blood supply, as is seen in cases in which the brain swells. In any of these cases, without adequate oxygen, a biochemical cascade called the ischemic cascade is unleashed, and the cells of the brain can die within several minutes. This type of injury is often seen in near-drowning victims, in heart attack patients, or in people who suffer significant blood loss from other injuries that decrease blood flow to the brain. All of these result in neurodegeneration, which is the progressive loss of neurons in the brain.

Spinal Cord Injury—Common causes of spinal cord injury include fractures of the vertebrae, which can damage the spinal cord from the concussive effect of injury due to displaced bony fragments, or damaged blood vessels, or contusion of emerging nerve roots. Dislocation of vertebrae can also cause spinal cord damage; dislocation is often the result of the rupture of an intervertebral disk, and may result in partial or complete severance of the spinal cord. Penetrating wounds can also cause severance or partial severance of the cord. Epidural hemorrhage and spinal subdural hematoma can result in progressive paraparesis due to pressure on the spinal cord. Examples of indirect injury to the spinal cord include damage induced by a blow to the head or a fall on the feet. Intramedullary injury can be the result of direct pressure on the cord or the passage of a pressure wave through the cord, laceration of the cord by bone, or the rupture of a blood vessel during the passage of a pressure wave through the cord with a hemorrhage into the cord. Intramedullary bleeding and hematoma formation can also be caused by rupture of a weakened blood vessel. Ischemic damage can occur following compression of the anterior spinal artery, pressure on the anastomotic arteries, or damage to major vessels (Gilroy, in Basic Neurology, McGraw-Hill, Inc. New York, N.Y. (1990).

Degenerative Diseases of the Nervous System

Alzheimer's Disease—Alzheimer's disease (AD), the most common type of dementia, is a neurodegenerative disease characterized by progressive cognitive deterioration together with declining activities of daily living and neuropsychiatric symptoms, or behavioral changes. The most obvious early symptom is loss of short-term memory, which usually manifests as minor forgetfulness that becomes steadily more pronounced, with relative preservation of older memories. As the disease progresses, cognitive impairment extends to language, skilled movements, recognition, and functions such as decision-making and planning. The pathological process consists primarily of neuronal loss or atrophy, mainly in the temporoparietal cortex, but also in the frontal cortex, together with an inflammatory response to the deposition of amyloid plaques and neurofibrillary tangles.

Frontoternporal dementia (FTD)—describes a clinical syndrome associated with shrinking of the frontal and temporal anterior lobes of the brain (formerly known as Pick's disease). The current designation of the syndrome groups together Pick's disease, primary progressive aphasia, and semantic dementia as FTD. Some doctors propose adding corticobasal degeneration and progressive supranuclear palsy to FTD and calling the group Pick Complex. There is a strong genetic component to the disease and FTD often runs in families.

Parkinson's Disease—is caused by the progressive impairment or deterioration of neurons in an area of the brain known as the substantia nigra. When functioning normally, these neurons produce a vital brain chemical known as dopamine. Dopamine serves as a chemical messenger allowing communication between the substantia nigra and another area of the brain called the corpus striatum. This communication coordinates smooth and balanced muscle movement. A lack of dopamine results in abnormal nerve functioning, causing a loss in the ability to control body movements. The compositions and methods of the present invention are effective in treating Parkinson's disease.

Huntington's disease (HD)—results from genetically programmed degeneration of neurons in certain areas of the brain. This degeneration causes uncontrolled movements, loss of intellectual faculties, and emotional disturbance. HD is a familial disease, passed from parent to child through a mutation in the normal gene. Some early symptoms of HD are mood swings, depression, and irritability, learning new things, remembering a fact, or making a decision. As the disease progresses, concentration on intellectual tasks becomes increasingly difficult and the patient may have difficulty feeding himself and swallowing. The rate of disease progression and the age of onset vary from person to person.

Motor Neuron Diseases

Amyotrophic lateral sclerosis (ALS)—sometimes called Lou Gehrig's disease, is a progressive, fatal neurodegenerative disease caused by the degeneration of motor neurons. ALS is marked by gradual degeneration of the neurons in the CNS that control voluntary muscle movement. The disorder causes muscle weakness and atrophy throughout the body. In ALS, both the upper motor neurons and the lower motor neurons degenerate or die, ceasing to send messages to muscles. Unable to function, the muscles gradually weaken and atrophy. Eventually, the brain completely loses its ability to initiate and control voluntary movement. The disease does not necessarily debilitate the patient's mental functioning in the same manner as Alzheimer's disease or other neurological conditions do. Instead, those suffering advanced stages of the disease may retain the same memories, personality, and intelligence they had before its onset.

Spinal muscular atrophy (SMA)—is a genetic, motor neuron disease caused by progressive degeneration of motor neurons in the spinal cord. The disorder causes weakness and wasting of the voluntary muscles. Weakness is often more severe in the legs than in the arms. The childhood SMAs are all autosomal recessive diseases. This means that they run in families and more than one case is likely to occur in siblings or cousins of the same generation.

Progressive bulbar palsy—is a disorder in which the nerves controlling the muscles of chewing, swallowing, and talking are affected, making these functions increasingly difficult. Because swallowing is difficult, food or saliva is often inhaled (aspirated) into the lungs, causing choking or gagging and increasing the risk of pneumonia. Death, which is often due to pneumonia, usually occurs 1 to 3 years after the disorder begins.

Primary Lateral Sclerosis and Progressive Pseudobulbar Palsy—are rare, slowly progressive variants of amyotrophic lateral sclerosis. Primary lateral sclerosis affects mainly the arms and legs, and progressive pseudobulbar palsy affects mainly the muscles of the face, jaw, and throat. Emotions may be changeable. Inappropriate emotional outbursts are common. In both disorders, severe stiffness accompanies muscle weakness. The disorders usually progress for several years before total disability results.

Peripheral Diseases

Peripheral neuropathy, in its most common form, causes pain and numbness in the hands and feet. The pain typically is described as tingling or burning, while the loss of sensation often is compared to the feeling of wearing a thin stocking or glove. Peripheral neuropathy can result from such problems as traumatic injuries (i.e. axotomy distal to the dorsal root ganglia) or surgical incisions, compression of nerves (i.e. Tic douloureux), post-herpetic infections (i.e. herpes zoster infection), HIV infection, metabolic problems (i.e. diabetes), hereditary sensory and autonomic neuropathies, exposure to toxins (i.e. neurotoxic chemotherapy induced peripheral neuropathy), and drugs (i.e. antiretroviral drugs).

Other disease, disorders and injuries that may benefit from the compositions and methods of the invention include ischemia and reperfusion injury, lung injury and fibrosis, hearing loss due to antibiotics or loud noise, acute respiratory distress syndrome (ARDS), diabetes, kidney disease, cardiovascular disease, and wound healing.

EXAMPLES

The following examples are put forth so as to provide those of ordinary skill in the art with a complete disclosure and description of how to make and use the compositions and methods of the invention, and are not intended to limit the scope of what the inventors regard as their invention. Efforts have been made to ensure accuracy with respect to numbers used (e.g., amounts, temperature, etc.) but some experimental errors and deviations should be accounted for. Unless indicated otherwise, parts are parts by weight, molecular weight is average molecular weight, temperature is in degrees centigrade, and pressure is at or near atmospheric.

Detailed information and methods on the preparation of AMP cell compositions, generation of ACCS, generation of pooled ACCS, detection of cytokines in non-pooled and pooled ACCS using ELISA, generation of PCS compositions, and generation of sustained-release CFS compositions can be found in U.S. Pat. Nos. 8,058,066 and 8,088,732, both of which are incorporated herein by reference.

Example 1

Evaluation of the Effect of ACCS on Apoptosis in Jurkat Cells

Apoptosis is programmed cell death and is a necessary event for proper healing and tissue turnover involving a complex network of biochemical pathways. Dis-regulation of apoptosis is a cause of delayed wound healing as well as many chronic diseases.

Depending on the extent of damage, cells will either apoptose or survive. Applicants have discovered that ACCS contains anti-apoptotic factors that may help some cells survive various insults that would typically lead to apoptosis. From a therapeutic perspective, these anti-apoptotic factors may benefit partially damaged cells such as those found in a wound by helping them survive and repopulate the wound bed quicker.

Initial experiments were performed using a FITC Annexin V staining kit (BD Biosciences) and analyzed by Flow Cytometry.

Brief description of the assay: In apoptotic cells, the membrane phospholipid phosphatidylserine (PS) is translocated from the inner to the outer part of the plasma membrane. Annexin V is a 35-36 kDa $Ca^{2+}$-dependent phospholipid-binding protein and has a high affinity for PS, thus it will bind to cells with exposed PS on the outer part of the plasma membrane. Since externalization of PS occurs in the earlier stages of apoptosis, FITC Annexin V staining can identify cells in the early stages of apoptosis. Membranes of dead and damaged cells are permeable to propidium iodide PI. For example, cells that are considered viable are FITC Annexin V and PI negative; cells that are in early apoptosis are FITC Annexin V positive and PI negative; and cells that are in late apoptosis or are already dead are both FITC Annexin V and PI positive.

Initial experiments were done using Jurkat cells cultured in RPMI medium containing 10% FCS and antibiotic. Approximately $2 \times 10^6$ Jurkatcells were treated overnight with 12 μM camptothecin, an apoptosis inducer, and 1×, 2× or 4×ACCS treatment or control media and then stained the next day with Annexin V.

Results—In cells treated with camptothecin only, the percentage of apoptotic cells was 48.2%, whereas untreated controls were 6.6% apoptotic. In the presence of both ACCS (1×, 2× or 4×) and camptothecin, the percentage of apoptotic cells was reduced to approximately 11%. While the percentage of apoptotic cells was reduced in the presence of ACCS, it did not seem to be dose-dependent at the tested doses.

Example 2

Evaluation of the Effect of ACCS on Apoptosis in Human Foreskin Fibroblasts Cells Additional experiments were performed using an apoptosis assay kit which tests for the activation of both caspase 3 and caspase 7, both of which are key biomarkers of apoptosis.

Brief description of the assay: The Caspase-Glo® 3/7 Assay (Promega) provides a luminogenic caspase-3/7 substrate, which contains the tetrapeptide sequence DEVD, in a reagent optimized for caspase activity, luciferase activity and cell lysis. Following caspase cleavage, a substrate for luciferase (aminoluciferin) is released, resulting in the luciferase reaction and the production of light. The higher the luminescence the more caspase activity in the sample.

In this particular experiment, Human Foreskin Fibroblasts (HFF's) (~20,000 cells/well) were plated in 96-well plates and then treated for 5 hrs with and without Staurosporine, an apoptosis inducer, in control media, ACCS, irradiated ACCS, or normal growth media. Substrate was added and the luminescence was read on a Biotek plate reader.

Results—In the presence of either ACCS or irradiated ACCS, the caspase activation was significantly reduced. These results clearly indicate that there is a reduction in caspase activity with ACCS treatment compared to controls.

Example 3

Evaluation of the Effects of ACCS on Radiation Protection in Jurkat Cells

Based on the above results, it was hypothesized that ACCS may protect cells from exposure to radiation, a known apoptosis inducer. Experiments were performed using Jurkat Cells to evaluate the potential of ACCS as a radioprotection agent. In one such experiment, in a total volume of 1 mL, $2 \times 10^6$ Jurkat cells were irradiated at 1000, 2000 and 4000 RADs and apoptosis was analyzed by flow cytometry with Annexin V and the caspase luminescence assays. Treatments included control medium at 0.75× and ACCS at 0.75×. All treatments were added immediately prior to irradiating the cell samples.

Results—The results indicate that ACCS protects cells from ionizing radiation as indicated by a reduction (6.6, 19.4 and 18.2% reduction, respectively, for each irradiation dose as compared to control) in the percentage of apoptotic cells and a reduction (48, 42 and 25%, respectively, in caspase activity as compared to media controls) in the ACCS-treated samples.

Example 4

Evaluation of ACCS on Post-Irradiation Apoptosis in Jurkat Cells

An experiment was performed to confirm the prior results as well as to evaluate the effect of ACCS treatment post-irradiation. In this particular experiment, in a total volume of 1 mL, $2 \times 10^6$ Jurkat cells were irradiated at 2000 RADs. Apoptosis was analyzed by the caspase luminescence assay and viability was assessed by flow cytometry.

Results—In a previous experiment, protection with ACCS treatment was observed in Jurkat cells at 1000, 2000 and 4000 RAD's. The second experiment confirmed the first result and, compared to controls, protection was also observed 8 hrs post-ACCS treatment and increased viability of the irradiated Jurkat cells was seen in ACCS-treated cells.

In-vitro experiments were preformed to evaluate the ability of ACCS to protect cells when exposed to various inducers of apoptosis. Experiments on Jurkat cells using camptothecin as the induction agent and Annexin-V staining as a read-out demonstrated a protective effect of ACCS when compared to untreated control samples. Additional experiments on the same cell line with gamma irradiation as the inducer of apoptosis also showed protection by ACCS at 1000, 2000 and 4000 RADs. This protective effect was also seen when the ACCS was added several hours post irradiation exposure which suggests that ACCS may be a viable treatment for radiation sickness. ACCS's ability to protect cells from insult was also assessed on various cell lines including fibroblasts and HUVEC cells (data not shown). In all cases, under these test conditions, there was a measurable protective effect of ACCS treatment compared to the untreated controls, The experiments measured the caspase 3/7 activity with two different apoptosis inducers, camptothecin and staurosporine.

Example 5

Evaluation of the Effects of ACCS on Radiation Protection in Hematopoietic Stem and Progenitor Cells Based on the above results, it is hypothesized that ACCS may protect hematopoietic stem and progenitor cells from exposure to radiation. Experiments are performed using hematopoietic stem and progenitor cells to evaluate the potential of ACCS as a radioprotection agent in these cell types. In a representative experiment, in a total volume of 1 mL, $2 \times 10^6$ hematopoietic stem or progenitor cells are irradiated at 1000, 2000 and 4000 RADs and apoptosis is analyzed by flow cytometry with Annexin V and the caspase luminescence assays. Treatments include control medium at 0.75× and ACCS at 0.75×. In certain experiments, the treatments are added immediately prior to irradiating the cell samples. In other experiments, treatments are added after irradiating the cell samples.

Example 6

Evaluation of the Effects of AMP Cells on Radiation Protection in Hematopoietic Stem and Progenitor Cells Based on the above results, it is hypothesized that AMP cells may protect hematopoietic stem and progenitor cells from exposure to radiation. Experiments are performed using hematopoietic stem and progenitor cells to evaluate the potential of AMP cells as a radioprotection agent in these cell types. Hematopoietic stem or progenitor cells are irradiated and apoptosis is analyzed by flow cytometry with Annexin V and the caspase luminescence assays. Treatments include adding various concentrations of AMP cells at different time points. In certain experimental conditions, treatments are added immediately prior to irradiating the cell samples. In other experiments conditions, treatments are added post-irradiation of the cell samples.

Example 7

Detection of Anti-apoptotic Factors in ACCS

The following anti-apoptotic proteins were detected in ACCS by antibody array analysis: Bcl-2 (B-cell lymphoma 2), Bcl-w, CD40L (CD40 Ligand), cIAP-2, HSP60 (heat shock protein 60), HSP70 (heat shock protein 70), IGF-II (Insulin growth factor II), IGF-1sR (IGF-1 soluble receptor), Livin, P27 (cyclin Kinase inhibitor), Surivin, sTNF-R1, sTNF-R2, TRAILR-3, TRAILR-4.

In addition to the anti-apoptotic proteins listed above, TIMP-1, VEGF, Angiogenin, PDGF-BB, EGF and human serum albumin, detected by ELISA, also exhibit anti-apoptotic activity (Liu, Xu-Wen, et al. "Tissue inhibitor of metalloproteinase-1 protects human breast epithelial cells from extrinsic cell death: a potential oncogenic activity of tissue inhibitor of metalloproteinase-1." Cancer research 65.3 (2005): 898-906; Abu-Ghazaleh, Robin, et al. "Src mediates stimulation by vascular endothelial growth factor of the phosphorylation of focal adhesion kinase at tyrosine 861, and migration and anti-apoptosis in endothelial cells" Biochemical Journal 360.Pt 1 (2001): 255; Li, Shuping, Wenhao Yu, and Guo-Fu Hu. "Angiogenin inhibits nuclear translocation of apoptosis inducing factor in a Bcl-2-dependent manner" Journal of cellular physiology 227.4 (2012): 1639-1644; Steidinger, Trent U., David G. Standaert, and Talene A. Yacoubian. "A neuroprotective role for angiogenin in models of Parkinson's disease" Journal of neurochemistry 116.3 (2011): 334-341; Hsieh, Patrick C H, et al. "Controlled delivery of PDGF-BB for myocardial protection using injectable self-assembling peptide nanofibers." Journal of Clinical Investigation 116.1 (2006): 237-248; Shao, Hanshuang, Xiao-Ming Yi, and Alan Wells. "Epidermal growth factor protects fibroblasts from apoptosis via PI3 kinase and Rac signaling pathways" Wound Repair and Regeneration 16.4 (2008): 551-558; Zoellner, Hans, et al. "Serum albumin is a specific inhibitor of apoptosis in human endothelial cells" Journal of cell science 109.10 (1996): 2571-2580.

The present invention may be embodied in other specific forms without departing from the spirit or essential attributes thereof. Any equivalent embodiments are intended to be within the scope of this invention. Indeed, various modifications of the invention in addition to those shown and described herein will become apparent to those skilled in the art from the foregoing description. Such modifications are also intended to fall within the scope of the appended claims.

Throughout the specification various publications have been referred to. It is intended that each publication be incorporated by reference hi its entirety into this specification.

What is claimed is:

1. A method for reducing the number of apoptosis-induced cell deaths in a population of cells undergoing excessive cellular apoptosis, the method comprising the step of contacting the population of cells undergoing excessive cellular apoptosis with a therapeutically effective dose of a composition selected from the group consisting of Amnion-derived Cellular Cytokine Solution (ACCS) and Amnion-derived Multipotent Progenitor (AMP) cells, such that the number of apoptosis-induced cell deaths is reduced.

2. The method of claim 1 wherein the ACCS comprises physiologic concentrations of VEGF, TGFβ2, Angiogenin, PDGF, TIMP-1 and TIMP-2, wherein the physiologic concentration is about 5.0-16 ng/mL for VEGF, about 3.5-4.5 ng/mL for Angiogenin, about 100-165 pg/mL for PDGF, about 2.5-2.7 ng/mL for TGFβ2, about 0.68 μg/mL for TIMP-1, and about 1.04 μg/mL for TIMP-2.

3. The method of claim 1 wherein the excessive cellular apoptosis occurs in a subject as a result of a condition selected from the group consisting of a radiation-induced injury, and an injury to nervous tissue.

4. The method of claim 1 wherein the ACCS or AMP cells are administered in combination with another agent.

5. The method of claim 4 wherein the other agent is selected from the group consisting of cytokines, chemokines, growth factors, antibodies, inhibitors, antibiotics, anti-fungals, anti-virals, immunosuppressive agents, anti-oxidants, and cells.

6. A method of protecting a population of cells at risk for developing excessive cellular apoptosis, the method comprising the step of contacting the population of cells at risk for developing excessive cellular apoptosis with a therapeutically effective dose of a composition selected from the group consisting of ACCS and AMP cells, such that the cells are protected from developing excessive cellular apoptosis.

7. The method of claim 6 wherein the ACCS comprises physiologic concentrations of VEGF, TGFβ2, Angiogenin, PDGF, TIMP-1 and TIMP-2, wherein the physiologic concentration is about 5.0-16 ng/mL for VEGF, about 3.5-4.5 ng/mL for Angiogenin, about 100-165 pg/mL for PDGF, about 2.5-2.7 ng/mL for TGFβ2, about 0.68 μg/mL for TIMP-1, and about 1.04 μg/mL for TIMP-2.

8. The method of claim 7 wherein the protecting of cells from excessive cellular apoptosis occurs in a subject that is at risk of developing a condition selected from the group consisting of, a radiation-induced injury, and an injury to nervous tissue.

9. The method of claim 6 wherein the protecting of cells from excessive cellular apoptosis occurs in a donated organ or tissue.

10. The method of claim 6 wherein the ACCS or AMP cells are administered in combination with another agent.

11. The method of claim 10 wherein the other agent is selected from the group consisting of cytokines, chemokines, growth factors, antibodies, inhibitors, antibiotics, anti-fungals, anti-virals, immunosuppressive agents, anti-oxidants, and cells.

* * * * *